United States Patent [19]
Busack et al.

[11] Patent Number: 5,336,390
[45] Date of Patent: Aug. 9, 1994

[54] ELECTROCHEMICAL GAS SENSOR WITH DISK-SHAPED ELECTRODES, WHICH ARE ALSO ELECTRICAL CONTACT LEADS

[75] Inventors: Hans-Jürgen Busack; Klaus Karob; Bernd Lindner, all of Lübeck; Rudolf Gambert, Arfrade; Horst-Peter Bleichert, Böbs, all of Fed. Rep. of Germany

[73] Assignee: Drägerwerk AG, Lubeck, Fed. Rep. of Germany

[21] Appl. No.: 105,895

[22] Filed: Aug. 11, 1993

[30] Foreign Application Priority Data

Sep. 26, 1992 [DE] Fed. Rep. of Germany ....... 4232295

[51] Int. Cl.⁵ ............................................. G01N 27/26
[52] U.S. Cl. ...................... 204/431; 204/432; 204/412; 204/415; 204/408; 204/424
[58] Field of Search ............... 204/424, 431, 432, 408, 204/412, 415, 252, 253

[56] References Cited

U.S. PATENT DOCUMENTS 5,126,035  6/1992  Kiesele et al. .............. 204/415
5,183,550  2/1993  Mattiessen ................. 204/415

FOREIGN PATENT DOCUMENTS 2311096 10/1974  Fed. Rep. of Germany .
2075197 11/1981  United Kingdom .

*Primary Examiner*—John Niebling
*Assistant Examiner*—Bruce F. Bell
*Attorney, Agent, or Firm*—McGlew and Tuttle

[57] ABSTRACT

An electrochemical gas sensor for detecting gaseous components in the environment has a diffusion membrane, a measuring electrode, a counterelectrode, and, if desired, a reference electrode, pressed together in a disk stack, which are accommodated in a pot-shaped cover, which in turn is beaded around the sealing edge (6) of a housing pot (1). A compression spring (21) in the housing pot (1) presses a wick disk (20) against the measuring electrode (12), so that a constant and pressurized, intimate and sealed positioning of the disk stack is guaranteed. It is achieved as a result that no additional contact leads from the electrodes to the outer space of the sensor to the measuring and evaluating unit are needed, so that leakage-free sealing of the sensor to the outside is possible, and that a constantly stable, reproducible measured signal is obtained because of the defined and narrow electrolyte film on the surface of the measuring electrode.

12 Claims, 2 Drawing Sheets

ELECTROCHEMICAL GAS SENSOR WITH DISK-SHAPED ELECTRODES, WHICH ARE ALSO ELECTRICAL CONTACT LEADS

FIELD OF THE INVENTION

The present invention pertains to an electrochemical gas sensor for detecting gaseous components in a gaseous environment by means of a disk-shaped measuring electrode, wherein the gaseous components to be detected have access to the measuring electrode via a diffusion path, likewise designed as a disk, and with a counterelectrode, which is accommodated, together with the measuring electrode, in an electrolyte space filled with a measuring electrolyte within a sensor housing, which is designed as a housing pot, which is in electrical contact with the counterelectrode, and in which an electrolyte-impregnated wick is provided, and the wick is in contact, with a wick disk, with the electrolyte-side surface of the measuring electrode, which in turn is brought into electrical contact with a cover disk, which is located, as an outermost housing closure, toward the gas side, and is electrically separated from the sensor pot by a sealing ring.

BACKGROUND OF THE INVENTION

Such an electrochemical gas sensor has become known from British Patent Application No. GB-2 075 197 A.

The prior-art sensor has a housing pot, in the bottom of which the counterelectrode is accommodated and is in electrical contact with the housing pot, which is also filled with the electrolyte necessary for detecting the gas. The open edge of the housing pot is provided with a circumferential groove, pressed to the inside, on which an electrically insulating sealing ring with L-shaped cross section is placed. The inwardly projecting contact edge of the sealing ring is used to accommodate, in the order beginning from the electrolyte, first a wick disk, over which the disk-shaped measuring electrode is placed, and which latter is in turn covered with a polyfluoroethylene (PTFE) disk acting as a diffusion path. The closure is formed by a disk-shaped cover with a central hole for the access of the gaseous components to be detected. A metallic contact strip, whose length far exceeds the cross section of the sealing ring, is placed adjacent to the electrolyte-side, reaction-sensitive surface of the measuring electrode. After completion of the disk stack, whose closure is formed by the metallic cover, the edge of the housing pot is pressed around the disk tack, clamping same as a whole against the groove provided. The contact strip between the disk edges and the sealing edge is pressed upward in the direction of the metal cover and is folded over, so that it is brought into clamping connection with the measuring electrode surface, on the one hand, and with the metal cover, on the other hand. The housing pot forms one of the electrical contacts of the counterelectrode, and the cover disk forms the other electrical contact for the measuring electrode for connection to a measuring and evaluating unit. Depending on the composition of the electrolyte and the electrode materials used, the prior-art sensor can be used to detect various oxidizing or reducing gases. There are two different embodiments of the prior-art sensor, namely, a so-called two-electrode design, which has only the counterelectrode, besides the measuring electrode, and a so-called three-electrode design, which additionally has a reference electrode, which is maintained at a constant reference potential in relation to the measuring electrode via a potentiostat.

It was found disadvantageous with the prior-art gas sensor that despite the tight pressing, the contact strip placed around the disk stack releases only a small capillary section, through which the electrolyte can penetrate to the closing disk, thus forming, as it were, a short-circuit section, at which a gas/electrolyte-measuring electrode three-phase boundary, which is brought into contact with the counterelectrode, is formed. As a result, an active surface is formed, which, though being small, does distort the measurement result, and is superimposed to the sensor signal. The smaller the desired sensor current, the greater is this disturbing effect. In light of the current increasing miniaturization not only of the evaluating electronic unit but even of the gas sensors themselves, it is of particular significance for the sensors to operate at the lowest possible measuring current in order to reach a long life even in the case of a miniature sensor with small electrolyte reserve. Any interfering current, however small, exerts a measured value-distorting effect. Another disadvantage is the fact that when the edge of the housing pot is pressed onto the housing cover disk, the sensor stack is pressed into the hollow space of the housing pot, so that the individual disks will more or less bulge out, because they lack a central support. As a result, electrolyte films of different thickness are formed between the individual disks, and especially on the measuring electrode surface, so that different diffusion paths will be formed for the gas to be detected, or even very small air bubbles may be retained in the intermediate spaces. Both properties exert an unfavorable effect on the sensor behavior in terms of response time and long-term stability.

SUMMARY AND OBJECTS OF THE INVENTION

The primary object of the present invention is to improve an electrochemical gas sensor of the class described such that additional contact leads from the electrodes to the outer space of the sensor can be omitted, and that an even more intimate compaction of the disk stack in the electrode area leads to a constantly stable electrolyte film on the measuring electrode surface.

This object is attained in a two-electrode sensor by the cover being designed as a pot-shaped cover, projecting with its edge over the housing pot from the outside, and accommodating at least the diffusion path and the measuring electrode provided with a contact surface located at the electrode surface, and by the sealing ring being placed around a sealing edge forming the edge of the housing pot such that the electrical insulation between the cover and the housing pot is formed during the sealing clamping of the cover on the sealing edge, on the one hand, and the disk stack is put under pressure effect against the wick disk, on the other hand, wherein the said sealing disk is pressed against the disk stack by applying a compression spring supported between the wick disk and the housing pot, and by the cover edge being in contact with the contact surface of the measuring electrode, thus forming the contact point to the measuring and evaluating unit.

In a three-electrode sensor, the task is accomplished by the further characteristics that a disk-shaped reference electrode is arranged between the measuring electrode and the counterelectrode, and the reference electrode is provided with a contact edge, which extends over the edge of the housing pot and is placed in a sealing manner around same, and the sealing ring acts as an electrical insulation between the reference electrode and the housing pot; that the contact edge is separated from the cover by means of an insulating piece; and that a contact area is left free for the connection of the measuring and evaluating unit on the contact edge placed around the edge of the housing pot.

The advantage of the present invention is essentially the fact that the electrolyte space and the disk-shaped electrodes accommodated in the pot-shaped cover, as well as the diffusion path are hermetically sealed against the environment, without any separate contact leads passing through the housing wall or the cover, so that no creep paths are formed for the electrolyte, and it is unnecessary to take any additional sealing measures, whose results are always unsatisfactory. For mechanical assembly, it is sufficient to ensure that the disk stack is pressed firmly against the wick disk and consequently to establish the most intimate contact possible between the electrolyte film and the measuring electrode, without bulging and warping of the disks within the disk stack taking place. The disk stack is virtually pressed together by the spring force, on the one hand, and the counterpressure generated by the pot-shaped cover, on the other hand. The connection between the pot-shaped cover and the edge of the housing pot can be established by a screw connection, or, in a simple case, the cover edge is beaded with the edge of the sensor housing, in which case the sealing ring is pressed at the same time against the edge of the housing pot, which edge is designed as a beaded edge. The same process can be used in this case for sealing the cover and the housing as is used in the manufacture of round cells. Due to the individual disks, which form the electrodes and the wick disk, being pressed together firmly into a dense disk stack, it is possible to obtain a very weak sensor current for detecting the gaseous components to be investigated, because the diffusion paths are minimized. As a result, the same service life that can be reached with the prior-art gas sensors is obtained even with a smaller electrolyte reserve. One can thus speak of a round cell in terms of both the manner of assembly and the external dimensions.

Due to the intimate contact between the measuring electrode and the extensive surface of the pot-shaped housing cover, there also is a good thermal contact between the two components, because the housing cover may be made of a metallic, electrically conducting material. Since the sensor current is temperature-dependent, temperature variations between the electrolyte temperature (electrode temperature) and ambient temperature (gas temperature) are rapidly equalized. This enhances the temperature stability of the sensor and contributes to the stability of measurement.

Since, moreover, there is no specific contact point at the cover either, but the entire surface of the cover, including its cover edge pulled over the edge of the housing pot, is available for contact with an electrical contact, the user has a high level of freedom in introducing the sensor into a capsule, in which the site for accommodating the electrical contacts can be selected relatively freely. It is only in the case of the three-electrode sensor design that an additional contact surface is to be provided at the contact edge of the reference electrode, to which the electrode voltage must be applied.

To detect the variation in temperature, which influences the measurement result, for correcting the measured signal, a temperature-sensitive sensor element can be brought into thermal contact with the outer circumference of the sensor housing and of the cover, and this signal can be sent as a temperature signal to the measuring and evaluating unit. Due to its miniaturization, the round cell is adapted to variations in temperature substantially more rapidly than are the conventional, prior-art sensors.

The individual disks in the disk stack are sealed by applying a hot-melt adhesive to the edge area of the disks, so that electrolyte- and gas-tight connection is guaranteed between the individual disks, on the one hand, and the cover as well as the other sealing elements, on the other hand, as a consequence of the contact pressure applied to the disk stack. A sealing method as well as suitable adhesive films for this purpose are described in West German Offenlegungsschrift No. DE-OS 23 11 096, and they can be used for the sensor in question. Suitable adhesive films made of Hostaflon PFA are commercially available from the firm of Hoechst AG.

To prepare a good contact surface between the measuring electrode and the cover edge, it is advantageous to have a metallic contact edge extending along the outer circumference of the disk. This contact edge may be designed such that the measuring electrode is shaped in the form of a shell, so that the edge of the shell is in intimate contact with the inner wall surface of the cover. Elastic pressing of the cover against the contact edge is ensured by placing the disk stack into the cover and subsequently connecting the cover to the edge of the housing pot; this elastic pressure is further improved by beading the cover edge for placing the cover on the edge of the housing pot and fastening the cover thereto, and by the cover edge applying an additional pressure to the contact edge of the measuring electrode during beading.

To grant access to the gaseous components to be detected into the electrolyte space of the sensor, the cover is provided with entry openings, which are closed by a porous pressing disk, which is joined by the diffusion membrane acting as a diffusion path, which in turn is followed by the measuring electrode. Thus, together with the diffusion membrane and the measuring electrode, the pressing disk forms a stable cover following the contours of the housing cover, which can be adapted to various mechanical pressure effects.

According to one particularly advantageous embodiment of the wick, it is designed as a hollow body, which is filled with the electrolyte, on the one hand, and, on the other hand, contains the compression spring, which has an elastic disk which is in contact with the electrolyte-side surface of the wick disk. Thus, the electrolyte is delivered to the measuring-active surface of the measuring electrode only via the wick disk, as a result of which electrolyte transport takes place only due to diffusion of the electrolyte through the pores of the absorbent nonwoven material of the wick. The hollow body formed by the wick either may be closed on all sides, or it is formed by a shell of rectangular shape made of a nonwoven material web, so that two opposite sides are open, but one nonwoven surface of the shell forms the wick disk, which is in contact with the measuring electrode surface.

To facilitate unhindered transport and exchange of used electrolyte with the unused electrolyte from the electrolyte space, the elastic disk in contact with the wick disk is provided with a plurality of openings.

To accurately define the measuring-active surface of the measuring electrode, it is favorable to cover the wick disk with a separating disk toward the measuring electrode, so that only a limited, but accurately definable partial area of the wick disk will be left free in electrolyte contact with the measuring electrode.

Due to the measuring-active surface of the measuring electrode being completely covered by the wick disk and to the pressure on the entire disk stack being maintained, it is ensured that the charge transfer during the reaction of the gas to be detected at the electrode surface, and the mass transfer of the reaction products take place exclusively via a diffusion process, which is the rate-determining step. A competing convection transfer, which would otherwise lead to the formation of gas bubbles in the electrolyte layer on the measuring-active electrode surface, and thus would distort the measured signal, is thus effectively prevented.

A suitable measuring electrode is designed as a gold-plated nickel screen in the form of a shell, whose edge, acting as a contact surface, is in contact with the inner wall of the cover.

The individual disks of the disk stack are sealed against one another and the cover by means of hot-melt adhesive disks (PFA or FEP), and are pressed against one another.

Changes in the environmental pressure, as well as thermal effects and diffusion effects of disturbing gases must not lead to lifting off of the diffusion membrane from the active measuring electrode surface, nor to leakage. Thus, providing a pressure equalization system, which equalizes such changes, belongs to the state of the art. This is provided in the present invention simply by including a gas bubble in the hollow space formed by the wick. It is thus possible to eliminate the need for pressure equalization membranes provided according to the known state of the art, which require additional sealing measures in the sensor housing, and thus form potential leakage sites for the electrolyte, or diffusion paths for the entry of gas at an unintended site. The gas bubble itself now forms the compressible component of the electrolyte liquid, which can yield to the variations occurring in pressure and temperature.

One suitable form for the counterelectrode is considered to be a counterelectrode pressed in the form of a pressed granular material into the housing pot, in which case the granular material is enclosed in a contact screen, which is electrically connected to the housing pot via a contact point. The contact screen shall pass through the granular metallic material over the largest possible area and thus improve the electrical conductivity, which would otherwise be ensured only via the contact points of the individual components of the granular material, and would not therefore bring about an ideal conductivity connection. The contact screen is connected to the sensor housing in an electrically conducting manner via the contact point, i.e., by spot welding, and thus it ensures improved removal of the current on the counterelectrode. It is advantageous in such an embodiment of the sensor for the compression spring to be clamped between the wick disk and the counterelectrode, so that it will not only exert the pressure on the disk stack in the sensor cover, but it will also ensure the increased contact pressure of the granular particles among each other as well as on the contact screen, on the one hand, and on the inner wall of the housing pot, on the other hand.

The electrochemical gas sensor described is suitable preferably for measuring oxygen in the ambient air, in which case the measuring electrode, being a cathode, consists of a gold-plated nickel screen, the electrolyte is a KOH solution, and the anode consists of a pressed granular lead part. If other electrode materials and electrolytes are selected correspondingly, it is also possible to measure other gaseous components with the same gas sensor.

If acid or corrosive electrolytes must be used to measure other gases, it is advantageous to provide the inner wall of the housing pot with a gold lining acting as a corrosion-resistant coating.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DETAILED DESCRIPTION OF THE PREFERRED EMBODIMENT

Figure 1:
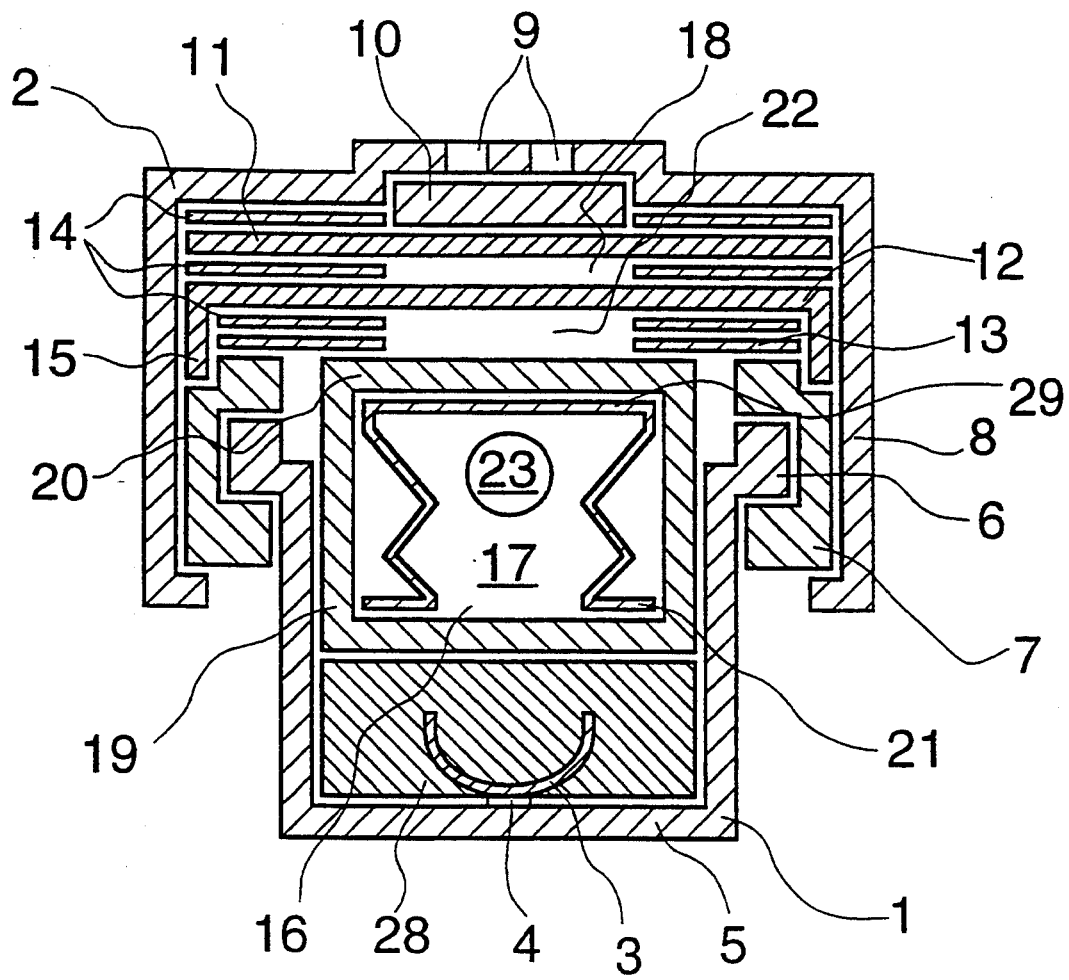
FIG. 1 is a sectional view through a two-electrode sensor according to the invention.

The sensor shown in FIG. 1 is used to detect oxygen in the ambient air. The assembly units of this sensor, which determine its external shape, form a housing pot 1, on the one hand, and a pot-shaped cover 2, on the other hand. A lead anode, made of pressed granular material, is located in the housing pot 1 as a counterelectrode 28. A pot-shaped contact screen 3, which is electrically connected to the bottom of the housing pot 1 by spot welding at a contact point 4, is placed into the lead anode. The housing pot 1 is made of a metallic deep-drawn part and thus forms the anode contact on its entire outer surface. The housing pot 1 is of cylindrical shape, so that a sealing edge 6, located opposite the pot bottom 5, has a circular circumference. The sealing edge 6 is set off to the outside from the rest of the housing pot 1, and is used to accommodate a sealing ring 7. The cover 2, whose cover edge 8, surrounding the sealing ring 7, is beaded around the sealing edge 6, is pulled over the housing pot 1, surrounding the sealing ring 7 and the sealing edge 6. The cover 2 accommodates a disk stack, which is composed, beginning from the gas inlet openings 9 facing the environment, of a pressing disk 10, a diffusion membrane 11, a measuring electrode 12, and a separating disk 13. The circular disk stack is sealed off toward the metallic cover 2, on the one hand, and, on the other hand, among the individual disks by means of hot-melt adhesive films 14 acting as a seal, and acting to hold together the circular disk stack. The measuring electrode 12 has, at its outer circular circumference, a contact surface 15, which, extending all around, is brought into electrical and thermal contact with the cover edge 8. Both the separating disk 13 and the hot-melt adhesive films 14 acting as sealing disks are provided in their centers with an opening, which exposes the measuring-active surface of the measuring electrode 12 to an electrolyte 17 located in an electrolyte space 16, on the one hand, and, on the other hand, generates an electrolyte layer 18 formed between the diffusion membrane 11 and the measuring electrode 12. The diffusion membrane 11 is permeable to oxygen, and impermeable to the electrolyte 17. The measuring electrode 12 (cathode), which is likewise permeable to the electrolyte, is formed of a perforated plate made of gold-plated nickel, which is pulled up at its outer edge to the contact surface 15 in the form of a shell. A wick 19 of rectangular shape, made into a hollow body, whose two visible surfaces are open in FIG. 1, is located in the electrolyte space 16. The wick 19 is formed of a nonwoven-like knit material and has a wick disk 20, directed toward the measuring electrode 12. The hollow body 19 is tensioned by a compression spring 21 and presses with its elastic disk 29 the wick disk 20 firmly against the measuring electrode 12, being maintained at a spaced location herefrom only by the separating disk 13 and the sealing disk 14 located therebetween. The annular separating disk 13 leaves free another electrolyte layer 22, which is filled with the electrolyte 17. A gas bubble 23 is included in the hollow body 19.

The individual parts represented in the drawing are shown at spaced locations from one another in order to make it possible to distinguish them from one another, but the disk stack is obviously intimately connected in the assembled state as a consequence of the sealing of the disk stack as well as the beading of the cover edge 8 around the sealing edge 6 and the resulting pressing of the sealing ring 7. The pressing effect is brought about by the cover 2, on the one hand, and, on the other hand, by the compression spring 21, which is supported between the wick disk 20 and the housing pot 1. The distances shown thus disappear, and the electrolyte layers 18, 22 are compressed to a few micrometers. The pressing disk 10 ensures both flat contact of the diffusion membrane 11 and a uniform lateral distribution of the amount of gas entering through the gas inlet openings 9.

Figure 2:
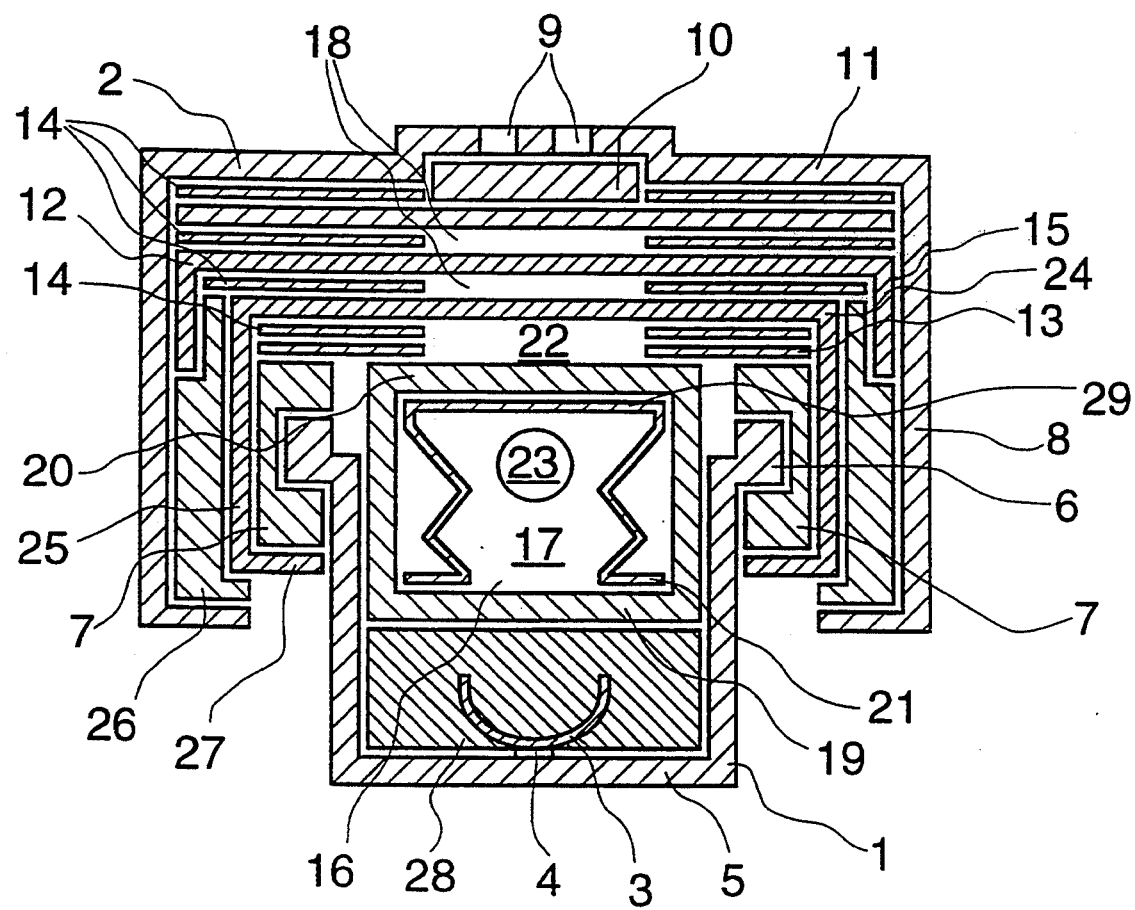
FIG. 2 is a sectional view through a three-electrode sensor according to the invention.

All components of the sensor shown in FIG. 2 are identical to those shown in FIG. 1, the difference being that another reference electrode 24 is accommodated in the disk stack between the measuring electrode 12 and the wick disk 20. Identical components which are also present in FIG. 1 are therefore designated by the same reference numerals. The reference electrode 24 is also of disk-shaped design and extends essentially over the same extent as the measuring electrode 12. It is porous and therefore permits the passage of the electrolyte and the reaction products of the gas. The reference electrode 24 is provided with a contact edge 25, which is separated from the housing pot 1 and from the cover edge 8 both in a liquid-tight manner and electrically by the sealing ring 7, on the one hand, and by an insulating piece 26, on the other hand. The contact edge 25 is pulled over the sealing edge 6 of the housing pot 1, and it leaves free a contact area 27, which is used as an electrical contact terminal for applying an electric contact potential from the measuring and evaluating unit, not shown. Both the insulating piece 26 and the cover edge 8 are beaded over the sealing edge 6 of the housing pot 1. The dimensioning of the individual components to be clamped around during beading is adjusted such that a uniform circumferential beaded edge will be formed. Thus, the cross section of the sealing ring 7 shown in FIG. 2 is different from that shown in FIG. 1, and the contact edge 25 extends around the sealing edge 6, and the other components in a circularly symmetrical housing pot 1 and cover 2 also extend around the entire circumference of the housing pot 1, just as in the case of the assembly units according to FIG. 1.

While a specific embodiment of the invention has been shown and described in detail to illustrate the application of the principles of the invention, it will be understood that the invention may be embodied otherwise without departing from such principles.

What is claimed is:

1. An electrochemical gas sensor for detecting gaseous components in a gaseous environment with a disk-shaped measuring electrode, comprising:

a pot-shaped sensor housing having a sealing edge;

a counterelectrode positioned within said sensor housing in electrical contact with said sensor housing;

a pot-shaped cover including a cover edge projecting over said pot-shaped sensor housing;

diffusion path means including an opening in said pot-shaped cover and a diffusion membrane;

a measuring electrode including a contact surface forming a part of an electrode surface of said measuring electrode, said measuring electrode being positioned between said cover and said housing;

a sealing ring positioned around said sealing edge of said pot-shaped sensor housing, said sealing ring establishing electrical insulation between said cover and said pot-shaped sensor housing upon a sealing clamping of said cover on said sealing edge;

an electrolyte filled electrolyte space including an electrolyte impregnated wick including a wick disk positioned between said cover and said housing in contact with an electrolyte-side surface of said measuring electrode;

said measuring electrode and said diffusion membrane each being formed as a disk and cooperating with a sealing disk and/or a pressing disk to form a disk stack, said wick disk being positioned adjacent an electrolyte side surface of said measuring electrode;

a compression spring supported between said wick disk and said pot-shaped sensor housing to press said disk stack, said cover edge being in contact with said contact surface of said measuring electrode to form a contact point.

2. An electrochemical gas sensor according to claim 1, further comprising:

a disk-shaped reference electrode including a contact edge extending beyond said pot-shaped sensor housing edge, sealingly thereabout, said disk-shaped reference electrode being positioned between said measuring electrode and said counterelectrode, said sealing ring acting as an electrical insulation between said disk-shaped reference electrode and said pot-shaped sensor housing;

an insulation piece separating said cover from said disk-shaped reference electrode contact edge, a contact area connected to said contact edge providing access to said contact edge around said edge of said pot-shaped sensor housing.

3. An electrochemical gas sensor according to claim 1, wherein:

said measuring electrode contact surface is designed as a metallic border extending at an outer circumference of said measuring electrode disk.

4. An electrochemical gas sensor according to claim 1, wherein:
said cover is provided with inlet openings for gas to be detected, a porous pressing disk being joined by said diffusion membrane acting as said diffusion path means, said diffusion membrane being followed by said measuring electrode in said disk stack.

5. An electrochemical gas sensor according to claim 1, wherein:
said wick is designed as a hollow body filled with said electrolyte, said compression spring being positioned in said hollow body, said compression spring including an elastic disk in contact with an electrolyte-side surface of said wick disk.

6. An electrochemical gas sensor according to claim 5, wherein:
said elastic disk is provided with a plurality of openings.

7. An electrochemical gas sensor according to claim 1, wherein:
said wick disk is covered on a measuring electrode side with a separating disk, said separating disk leaving free only a partial area of said wick disk in an electrolyte contact with said measuring electrode.

8. An electrochemical gas sensor according to claim 1, wherein:
said measuring electrode is formed as a gold-plated nickel screen having a shell shape with said edge in contact, as a contact surface, with an inner wall of said cover.

9. An electrochemical gas sensor according to claim 1, wherein:
disks of said disk stack are sealed against one another by means of hot-melt adhesive disks (PFA or FEP) and are pressed against each other.

10. An electrochemical gas sensor according to claim 5, wherein:
a gas bubble is provided in said hollow body of said wick.

11. An electrochemical gas sensor according to claim 1, wherein:
said counterelectrode is formed of pressed granular metal and is positioned in a bottom of said pot-shaped housing part, a contact screen being provided in said pressed granular metal and positioned electrically connected to said pot-shaped housing via a contact point.

12. An electrochemical gas sensor according to claim 1, wherein:
said inner wall of said pot-shaped sensor housing is provided with a gold lining.

* * * * *

UNITED STATES PATENT AND TRADEMARK OFFICE
CERTIFICATE OF CORRECTION

PATENT NO. : 5,336,390

DATED : August 9, 1994

INVENTOR(S) : Busack et al.

It is certified that error appears in the above-identified patent and that said Letters Patent is hereby corrected as shown below:

On title page, the
name of the second named inventor should read as follows:

[75] Inventors: Klaus Kaross

Signed and Sealed this

Eighth Day of November, 1994

*Attest:*

BRUCE LEHMAN

*Attesting Officer*      *Commissioner of Patents and Trademarks*